United States Patent [19]
DiSpirito et al.

[11] Patent Number: 5,898,003
[45] Date of Patent: Apr. 27, 1999

[54] METHOD AND MEANS FOR COLLECTING ODORS FROM A WASTE WATER LAGOON

[75] Inventors: Alan A. DiSpirito, Ames; James A. Zahn, Ankeny, both of Iowa

[73] Assignee: Iowa State University Research Foundation, Inc., Ames, Iowa

[21] Appl. No.: 08/879,393

[22] Filed: Jun. 20, 1997

Related U.S. Application Data

[63] Continuation-in-part of application No. 08/673,626, Jun. 26, 1996, Pat. No. 5,766,551.

[51] Int. Cl.⁶ ..................................................... G01N 1/22
[52] U.S. Cl. ..................... 436/181; 73/19.01; 73/19.12; 73/23.34; 73/863.21; 422/83; 422/88; 422/101; 422/102; 588/260; 436/178
[58] Field of Search ..................................... 436/177, 178, 436/181; 422/83, 88, 93, 94, 99, 101, 102, 104; 588/260; 73/19.01, 19.09, 19.1, 19.12, 23.34, 31.02, 31.03, 863.21, 863.23, 863.81, 866.5

[56] References Cited

U.S. PATENT DOCUMENTS

| | | |
|---|---|---|
| 3,198,000 | 8/1965 | Schlageter . |
| 3,800,595 | 4/1974 | Vincent . |
| 3,839,902 | 10/1974 | Scott et al. ................................ 73/61 |
| 4,863,692 | 9/1989 | Plumb ........................................ 31/22 |
| 4,919,892 | 4/1990 | Plumb ........................................ 33/28 |

*Primary Examiner*—Jan Ludlow
*Attorney, Agent, or Firm*—Zarley, McKee, Thomte, Voorhees & Sease

[57] ABSTRACT

An odor collection station for a waste water lagoon with a buoyant housing having a top, open bottom, and opposite side and end walls. The housing having a U-shaped duct with an upper and lower passageway connected by a vertical passageway. Buoyant elements secured to the housing maintain the lower passageway at a level higher than the water surface. Compressed air forced through an inlet port of the lower passageway combines with odors that rise from the lagoon surface and are pumped through the vertical and upper passageway to an outlet port where odor components are contained, measured, and analyzed.

5 Claims, 2 Drawing Sheets

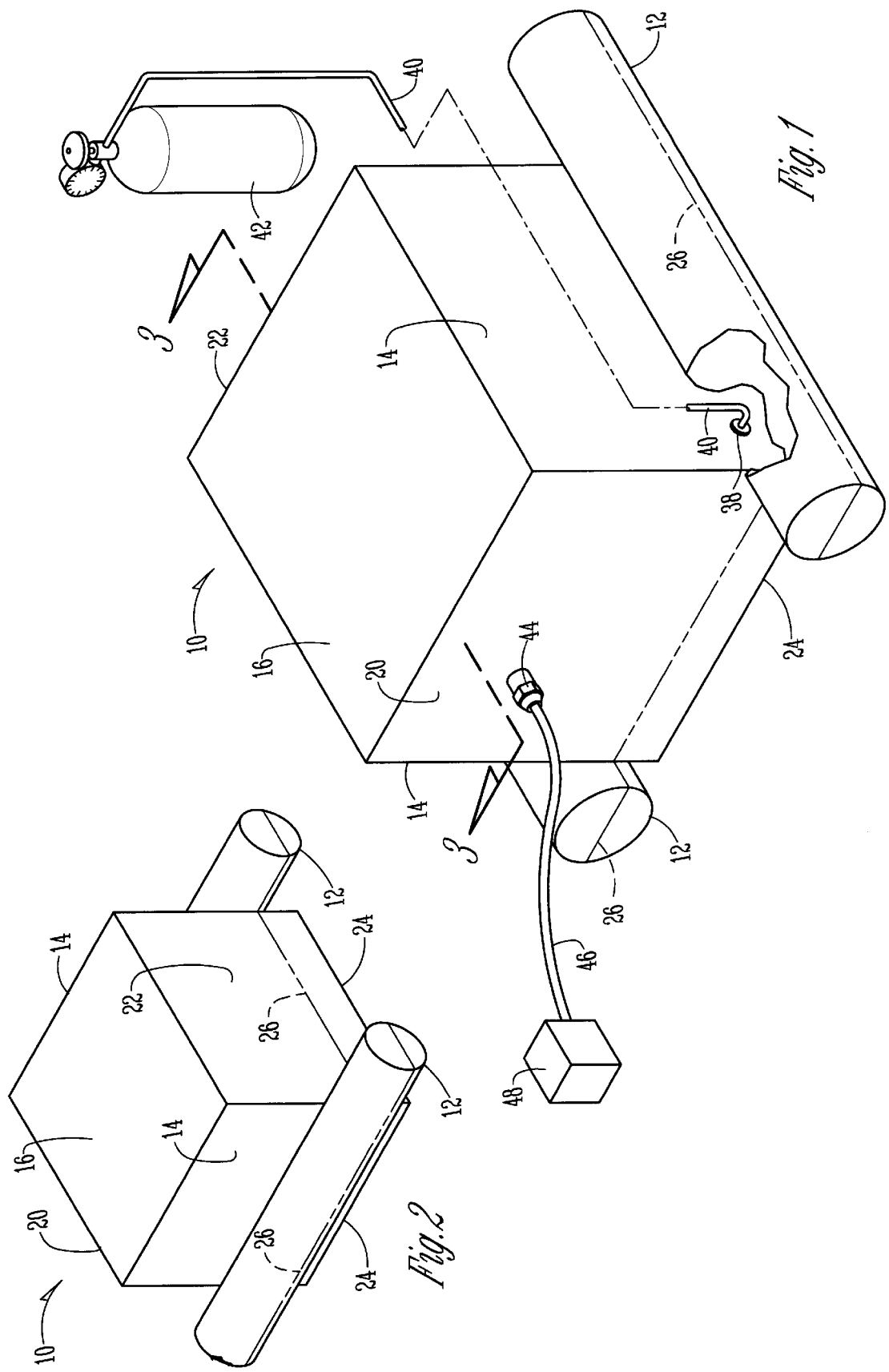

METHOD AND MEANS FOR COLLECTING ODORS FROM A WASTE WATER LAGOON

CROSS-REFERENCE TO A RELATED APPLICATION

This application is a Continuation-In-Part of Ser. No. 08/673,626 filed Jun. 26, 1996 now U.S. Pat. No. 5,766,551.

BACKGROUND OF THE INVENTION

Processing of livestock wastes usually involves the collection and storage in deep above ground or pit holding sites. Unless an aeration system is used, the storage system becomes anaerobic and odors from the storage system and/or confinement building can become a problem. Over 200 different volatile compounds have been identified in air samples from livestock waste storage/treatment systems. Although several of these compounds are individually regulated by the federal law (i.e. Clean Air Act), taken as a group livestock odors are not regulated by federal laws. Air quality from livestock production facilities is controlled in many areas by state and local regulations such as providing minimum distance standards between anaerobic lagoons and residences or public lands.

To protect individuals living in the vicinity of livestock production facilities, as well as the owners of such facilities, odor emission guidelines at the state or local government level must be developed. However, before these guidelines can be enacted, standard methods of odor measurements must be developed. The lack of a standard method of odor measurement has also made evaluation of odor control methods/technologies impossible. The objective of this invention is to identify "indicator compounds" and develop a standard test for odor measurement. These indicator compounds will be used to develop a "Quantitative Chemical Odor Index".

Methods to monitor odors from livestock waste storage/treatment systems can be divided into three groups; (1) scentometric, (2) chemical analysis or (3) electronic methods. Scentometry is the standard method used to measure odors. Scentometric methods, such as olfactometry, determine odor levels by a forced-choice ascending concentration series, selecting the minimal or threshold concentration. Oflactometers work by dilution of air samples with clean filtered (charcoal filter) air. The odor threshold (initial detection concentration) is determined by a panel consisting of 3 to 10 individuals. Air samples (usually 32 liters) are taken from the target site in polyethylene or teflon bags. This method has the advantage of using the human nose as its detector. The nose is still the most sensitive detector to a number of the chemicals that constitute the characteristic odors associated with livestock wastes. However, the method is cumbersome and slow which makes field studies difficult. Olfactometry's reliance on the judgment of a panel also makes standardization difficult if not impossible.

Chemical analysis by gas chromatography techniques has the advantage of reproducibility, impartiality, and adaptability to field testing. The problem with this method is the variability in the concentration of individual compounds from one site to another. Other problems include: (1) the human nose is more sensitive than gas chromatography detectors, (2) the synergistic and antagonistic effects of different compounds are not considered; and (3) the initial equipment expense. Electronic detectors/sensors have the impartiality of chemical techniques and the ability to measure complex mixtures as a group, like the human olfactory system. Unfortunately, electronic methods require standardization by both olfactometry and by chemical analysis.

One object of this invention is to provide a method of measuring odor emissions to establish standardized guidelines from waste water lagoons.

Another object of this invention is to provide a means of notifying owners and individuals living in the vicinity of livestock production facilities of potentially harmful odor emission levels.

Another object of this invention is to provide an efficient, easy, and prompt method for determining odor emission compounds and levels.

Another object of this invention is to provide an impartial, adaptable, and reproducible method for determining odor emission compounds.

Another object of this invention is to provide a means of measuring the odor emission of complex mixtures in varying concentrations as a group, considering both the synergistic and antagonistic effects between multiple compounds.

Another object of this invention is to provide an apparatus that is economical to manufacture and resistant to environmental elements.

These and other objects, features, and advantages of the present invention will become more apparent with reference to the accompanying specification and claims.

SUMMARY OF THE INVENTION

The invention, an odor collection station for a waste water lagoon, satisfies the problems in the art. The station is a buoyant housing that has a top, opposite side, and opposite end walls. The bottom of the housing is open, into which odors from the waste water lagoon rise.

In the housing is a substantially horizontal U-shaped duct having horizontally disposed spaced upper and lower passageways. The passageways extend from one end of the housing and are connected at the opposite end by a vertical passageway. The U-shaped duct has an internal closed compartment between the upper and lower passageway which maximizes carrier flow over the surface of the sampling area.

Buoyant elements are secured to the housing and when placed in the lagoon, maintain the housing at a level where the lower passageway remains above the top surface of the lagoon.

The lower passageway has an air inlet port at one end, and is connected to a source of compressed air. The upper passageway has an air outlet port at one end that is connected to an air sampling pump.

Extending laterally across the end of the lower passageway is a perforated pipe. The perforated pipe is connected to the inlet port through which air is compressed, exiting the perforations and forcing air through the lower passageway.

When the enclosed housing floats on a lagoon, odors are collected by forcing compressed air into one end of the lower passageway and thence in a reverse direction through said upper passageway to an outlet port connected to an air sampling pump where the odors are analyzed and measured.

BRIEF DESCRIPTION OF THE DRAWINGS

FIG. 1 is a front perspective view of the device of this invention;

FIG. 2 is an enlarged scale schematic rear perspective view of the device of this invention;

DESCRIPTION OF THE PREFERRED EMBODIMENT

Figure 3:
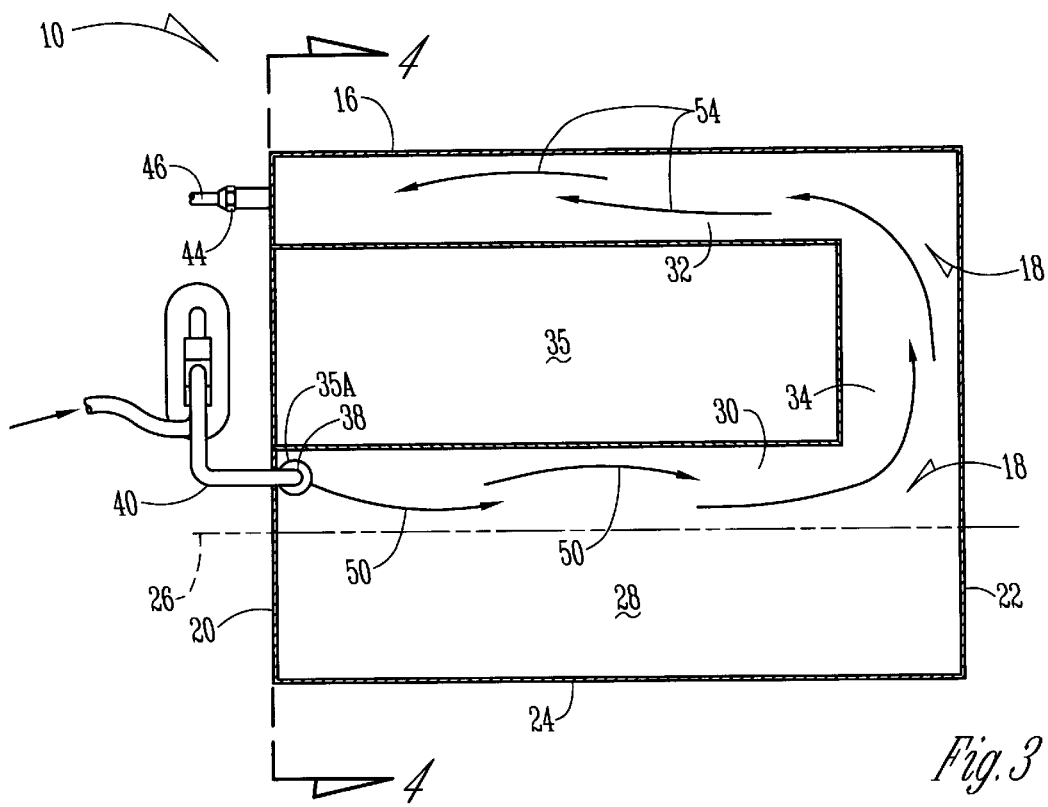
FIG. 3 is a sectional view taken on line 3—3 of FIG. 1.

A housing 10 has buoyant members 12, opposite sides 14, a top 16, an internal duct 18, and opposite ends 20 and 22. The buoyant members 12 are secured to the opposite sides 14. The buoyant members 12 maintain the bottom edge 24 of the housing 10 below lagoon surface 26 (waterline 26) to form a submerged compartment 28.

Within the housing 10 is a substantially horizontal U-shaped duct 18 having a lower passageway 30 which extends from one end 20 of housing 10 to the other end 22, and an upper passageway 32 which extends from one end 20 to the other end 22. The upper 32 and lower 30 passageways are connected at the other end 22 by a vertical passageway 34. Between the upper 32 and lower 30 passageways is an internal closed compartment 35.

Figure 4:
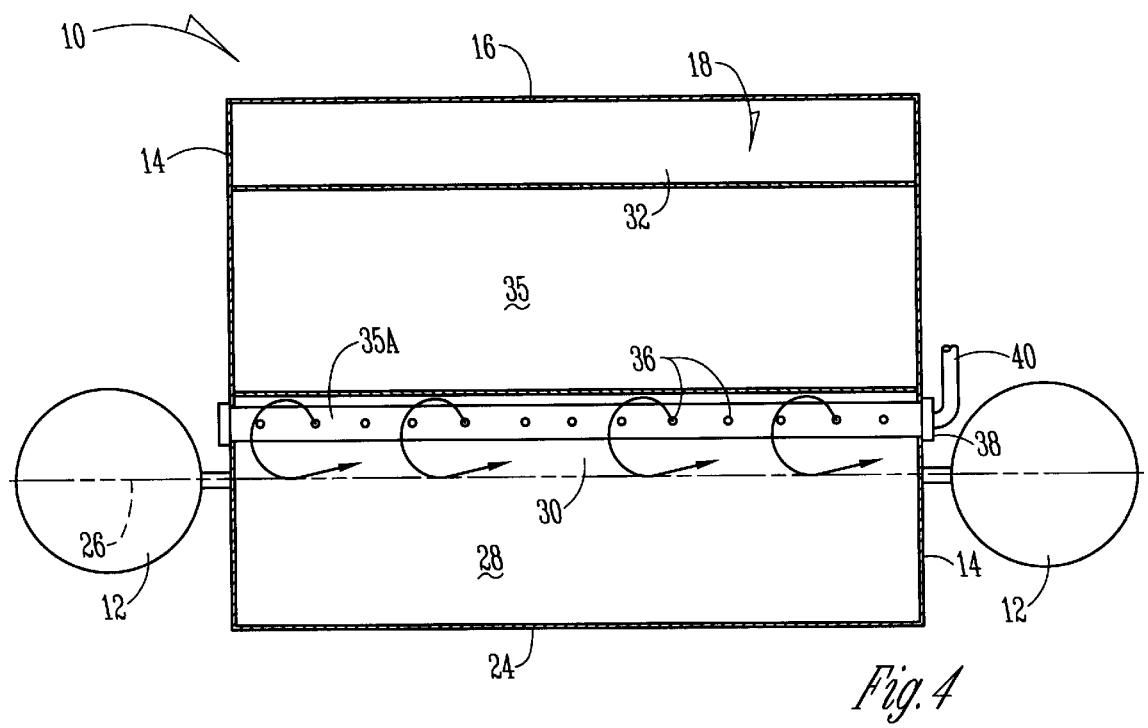
FIG. 4 is a sectional view taken on line 4—4 of FIG. 3.

A perforated pipe 35A extends laterally along one end 20 of housing 10 in the lower passageway 30 and has apertures 36 therein, and is connected to the compressed air inlet port 38. (FIGS. 1, 3 and 4).

The compressed air inlet port 38 is attached through a tube 40 to a source of compressed air 42. A compressed air outlet port 44 at end 20 of housing 10 in the upper passageway 32 is connected by pipe 46 to an air sampling pump 48.

The buoyant elements 12 secured to housing 10 maintain the lower passageway 30 at a height above the waterline 26. When air from the tank 42 is passed through the tube 40 to the perforated pipe 35A that is secured to the inlet port 38, air flows from one end of the lower passageway 30 to the other end as shown by the arrows 50 in FIG. 3. The enclosed rectangular compartment 35 maximizes the flow of the air over the surface of the sampling area. Odors from the sampling area rise from the water surface into the lower passageway 30. Along with the compressed air flowing through the lower passageway 30, the odors are pumped through the vertical passageway 34 and upper passageway 32 to the outlet port 44 by the air sampling pump 44. See arrows 54 in passageway 34, FIG. 3.

The buoyant members 12 and housing 10 are of a material that is resistant to environmental deterioration and are of a lightness such that they float in water or a managed waste lagoon.

It is therefore seen that this invention will accomplish at least all of its stated objectives.

We claim:

1. An odor collection station for a waste water lagoon,
   a buoyant housing having a top, an open bottom, opposite ends and opposite sides,
   a substantially horizontal U-shaped duct having horizontally disposed spaced upper and lower passageways extending from one end of said housing to said other end, and being connected by a vertical passageway at said other end,
   said U-shaped duct having an internal closed compartment, between the said upper and said lower passageways,
   buoyant elements secured to said housing to hold said housing at a high enough level to maintain said lower passageway at a height above the top surface of a waste water lagoon upon which said housing is floating,
   a compressed air inlet port in said lower passageway at said one end,
   a compressed air outlet port in said upper passageway at said other end,
   said inlet port connected to a source of compressed air, and
   said outlet port connected to an air sampling pump.

2. The device of claim 1 wherein said inlet port is connected to a perforated pipe in said lower passageway.

3. The device of claim 1 wherein said sampling pump is a vacuum pump.

4. A method of collecting odors from a waste water lagoon, comprising,
   floating an enclosed housing with an open bottom in a waste water lagoon,
   forming a lower air passageway in said housing in connection with the surface of said lagoon,
   forming an upper air passageway in said housing adjacent the top of said housing and connecting said upper and lower passages,
   forcing compressed air into one end of said lower passageway across the surface of the lagoon and thence in a reverse direction through said upper passageway to an outlet port,
   and connecting said outlet port to an air sampling pump.

5. A method of collecting odors from a waste water lagoon, comprising,
   floating an enclosed housing with an open bottom in a waste water lagoon,
   forming a lower air passageway in said housing in connection with the surface of said lagoon,
   forming an upper air passageway in said housing adjacent the top of said housing and connecting said upper and lower passageways,
   moving air across the surface of said lagoon inside said lower passageway, and thence in a reverse direction through said upper passageway to an outlet port,
   and thence pulling said moved air from said outlet port for odor sampling.

* * * * *